US005258019A

United States Patent [19]

Riddle et al.

[11] Patent Number: 5,258,019

[45] Date of Patent: * Nov. 2, 1993

[54] LUMBAR SPINE THERAPY DEVICE

[75] Inventors: George E. Riddle, Anderson County; George M. Cox, Campbell County; Ronnie J. Withrow, McMinn County; James L. Aslinger, Anderson County, all of Tenn.

[73] Assignee: United Apothecary, Inc., Oak Ridge, Tenn.

[ * ] Notice: The portion of the term of this patent subsequent to Jun. 23, 2009 has been disclaimed.

[21] Appl. No.: 902,084

[22] Filed: Jun. 22, 1992

Related U.S. Application Data

[63] Continuation-in-part of Ser. No. 640,945, Jan. 14, 1991, Pat. No. 5,123,916.

[51] Int. Cl.[5] .......... A61F 5/00

[52] U.S. Cl. .......... 606/242; 606/243; 606/245; 128/25 R

[58] Field of Search .......... 128/25 R, 25 C; 606/240, 241, 242, 243, 244; 200/61.93; 482/909

[56] References Cited

U.S. PATENT DOCUMENTS

| | | | |
|---|---|---|---|
| 1,190,195 | 7/1916 | Schmidt | 128/74 |
| 1,830,071 | 11/1931 | Patton | 128/72 |
| 2,002,349 | 5/1935 | Lundeen | 128/72 |
| 2,104,745 | 1/1938 | Howell et al. | 128/74 |
| 2,152,431 | 3/1939 | Jensen | 128/74 |
| 2,179,595 | 11/1939 | McManis | 128/74 |
| 2,598,204 | 5/1952 | Allen | 128/74 |
| 2,749,911 | 6/1956 | Griffin | 606/242 |
| 2,865,367 | 12/1958 | Sorenson | 128/71 |
| 2,931,354 | 4/1960 | Sellner | 128/25 |
| 3,241,828 | 3/1966 | Adolphson et al. | 128/72 X |
| 3,315,666 | 4/1967 | Sellner | 128/25 |
| 3,450,132 | 6/1969 | Ragon et al. | 128/25 |
| 3,623,480 | 11/1971 | Chisolm | 128/25 |
| 3,674,017 | 7/1972 | Stefani, Jr. | 128/25 R |
| 4,144,880 | 3/1979 | Daniels | 128/71 |
| 4,531,730 | 7/1985 | Chenera | 128/25 R |
| 4,649,905 | 3/1987 | Barnes | 128/74 |
| 4,655,200 | 4/1987 | Knight | 128/71 |
| 4,798,197 | 11/1989 | Nippoldt et al. | 128/25 R |
| 4,827,913 | 5/1989 | Parker | 128/25 R |
| 4,834,072 | 6/1989 | Goodman | 128/25 R |
| 4,869,494 | 9/1989 | Lambert, Sr. | 128/25 R |
| 4,888,581 | 12/1989 | Guscott | 200/61.93 |
| 4,890,092 | 12/1989 | Grimm | 200/61.93 |
| 4,900,014 | 2/1990 | DeGraff | 128/25 R |
| 4,953,541 | 9/1990 | Parker, Jr. | 128/25 R |
| 4,957,286 | 9/1990 | Persons, II et al. | 482/909 |
| 5,099,828 | 3/1992 | Duke | 128/25 R |
| 5,107,822 | 4/1992 | Ohashi | 128/25 R |
| 5,123,916 | 6/1992 | Riddle et al. | 606/242 |

*Primary Examiner*—Richard J. Apley
*Assistant Examiner*—Jeanne M. Mollo
*Attorney, Agent, or Firm*—Pitts & Brittian

[57] ABSTRACT

An improved lumbar spine therapy device (10) for passively exercising the muscle groups especially surrounding the lumbar spine for postoperative and other rehabilitative therapy such as to allow normal collagen formation to occur. A frame (12) is included for engaging a support surface (32). A body support (14) is provided for supporting the body a patient and includes a stationary support (64) for supporting the buttocks region of a patient a pivoting support (78) for supporting the torso and pivoting leg supports (220A,220B) for supporting the legs of a patient. A motor (92) is provided for driving at least one pivoting support oscillator (18), the oscillators (18) being provided to oscillate each pivoting support (78) independently. An amplitude adjuster (20) is connected to each oscillator (18) for altering the amplitude of displacement. A control box (22) is provided for carrying the motor controls, including at least a patient control button (24) and an emergency stop button (26). A restraining belt (28) is provided to prevent a patient from slipping along the body support (14). Casters (170) with locking wheels (172) are provided to aid in easy transporting the device (10).

14 Claims, 7 Drawing Sheets

LUMBAR SPINE THERAPY DEVICE

This application is a continuation-in-part and discloses and claims subject matter disclosed in our earlier filed pending application, Ser. No. 07/640,945 filed on Jan. 14, 1991, now U.S. Pat. No. 5,123,916 issued Jun. 23, 1992.

DESCRIPTION

1. Technical Field

This invention relates to the field of postoperative spinal therapy. Specifically, this invention relates to an apparatus used in the selective postoperative rehabilitation of the lumbar spine and/or hips to regain strength and function.

2. Background Art

In the field of postoperative spinal therapy, it is well known that serious loss of motion, painful contractures and stiffness may occur, particularly in the lumbar spine. It is also well known that rehabilitation is difficult in that the normal collagen formation cannot occur and disorganized scar results which further impedes the healing process and recovery.

Other devices have been produced to exercise the human body for rehabilitative or other purposes. Typical of the art are those devices disclosed in U.S. Pat. No. 2,152,431 issued to S. H. Jensen on Mar. 28, 1939; U.S. Pat. No. 2,598,204 issued to R. E. Allen on May 27, 1952; and U.S. Pat. No. 3,315,666 issued to J. W. Sellnor on Apr. 25, 1967; U.S. Pat. No. 3,450,132 issued to C. A. Ragon, et al. on Jun. 17, 1969; U.S. Pat. No. 3,623,480 issued to R. F. Chisholm on Nov. 30, 1971; U.S. Pat. No. 3,674,017 issued to H. Stefani, Jr. on Jul. 4, 1972; U.S. Pat. No. 4,531,730 issued to R. Chenera on Jul. 30, 1985; U.S. Pat. No. 4,827,913 issued to A. E. Parker on May 9, 1989; and U.S. Pat. No. 4,834,072 issued to L. M. Goodman on May 30, 1989. Each of these devices is designed to exercise the human body in some fashion for strengthening, stretching, relaxing, reducing weight, or some other related function. None of these, however, is designed specifically for exercising a patient's spine as a rehabilitation technique following surgery, or for patients suffering from chronic deconditioned spines. For example, the U.S. Pat. Nos. 3,623,480 ('480), 3,674,017 ('017), and 4,827,913 ('913) patents are most useful in exercising the abdomen region. However, these designs employ a single pivoting support surface, the surface being pivoted in a range from substantially the horizontal plane upward to substantially the vertical plane. The U.S. Pat. No. 4,834,072 ('072) patent discloses an invention which is specifically designed to exercise the legs in like manner by elevating the legs simultaneously or individually above or below the horizontal plane, with no other body parts being exercised. The U.S. Pat. No. 3,450,132 ('132) patent is designed to exercise the feet, legs, hips, back, arms, shoulders and neck of a patient suffering from polio or other form of paralysis or muscular disorder.

The desired exercise for postoperative spinal therapy begins with the patient lying in a substantially horizontal plane, the torso and head then being lowered to an angle below the horizontal as the legs are also lowered at the same rate and amplitude, the buttocks remaining stationary throughout. The torso and legs are then raised to the starting position and the processed repeated a desired number of times or for a desired duration. The U.S. Pat. Nos. 2,152,431 ('431), 3,315,666 ('666), and 4,531,730 ('730) patents disclose devices which may be used to acquire this type of motion, however, they are not designed specifically for the postoperative treatment of spinal patients and offer a much larger range of motion than is desired, along with other features unnecessary or inappropriate for such treatment. For example, the '666 patent is designed to massage a user's back or other body part, depending on how the device is employed, and requires the motion of the user to manipulate the device as opposed to an external power source. This, of course, is undesirable due to the weakened condition of the spinal patient. The '666 patent does not provide for a stationary buttocks support, thereby preventing the isolation of the desired muscles for rehabilitation. Likewise, the '730 patent is ineffective because it is designed specifically for stretching the legs of a user in order to improve leg flexibility. The '730 patent is also manually operated with no means for limiting the range of motion of each repetition.

It is sometimes desirable to concentrate treatment to the hip region of the patient, or to include treatment of this region along with the treatment of the lumbar spine. An effective method of treating the hip region includes alternately raising and lowering the legs, one leg being raised while the other is being lowered, and vice versa. In this type of therapy, it may be desirable to move the legs through a greater range of motion than the back. The devices disclosed in the U.S. Pat. Nos. 2,598,204 ('204), and 4,834,072 ('072) patents provide this type of exercise. However, the '204 patent requires separate drive means for oscillating the legs and the back. The '072 patent does not allow for the exercise of the lumbar spine.

Therefore, it is an object of this invention to provide a means for passively exercising the muscle groups especially surrounding the lumbar spine for postoperative and other rehabilitative therapy.

Another object of this invention is to provide a means whereby the normal collagen formation may occur, thus minimizing scarring and allowing a faster return to normal function and development of strength in both the muscles of function as well as the secondary support system.

It is also an object of this invention to provide a means whereby the upper body and lower body are simultaneously exercised.

Another object of this invention is to provide a means whereby the range of motion is independently selected for the upper and lower body.

Still another object of this invention is to provide a drive means to power both the upper body and lower body exercise means.

It is a further object of the present invention to provide a means whereby the legs of the patient may be exercised independently one from the other and the upper body.

Yet another object of this invention is to provide a means whereby the patient may control the operation of the device.

DISCLOSURE OF THE INVENTION

Other objects and advantages will be accomplished by the present invention which serves to passively exercise the muscle groups especially surrounding the lumbar spine for postoperative and other rehabilitative therapy. The lumbar spine therapy device includes a frame means for engaging a support surface. The frame means is fabricated from a lightweight, rigid material such as tubular steel or the like. In the preferred embodiment, the frame means has a substantially box-shaped configuration with a length and width to support a selected size body support means. The height of the frame means is dimensioned such that a patient may easily position his/her body on the body support means, or in the case of an inambulant patient, medical attendants may easily move the patient from a typical bed to the device.

The body support means is provided for supporting the body of a patient. The body support means includes at least one stationary support means and at least one pivoting support means. A first stationary support means is provided to support the buttocks region of the patient. The first stationary support means is connected to the frame means proximate the middle portion such that the stationary support means is elevated above the frame means. The stationary support means of the preferred embodiment has a substantially rectangular configuration and is dimensioned to comfortably seat a patient of a selected size. In the preferred embodiment, the stationary support includes a planar member with a cushion attached to the top side for the comfort of the patient, especially when extended use is required. A second stationary support means may be provided in an alternate embodiment for supporting at least a portion of the legs of a patient. The second stationary support means of this embodiment is substantially the same height as the first stationary support means and is further constructed similarly to the first stationary support means.

A first pivoting support means is provided for supporting at least the torso of a patient. A second pivoting support means may be provided for supporting at least the upper legs of a patient. The second pivoting support means is provided in circumstances where it is desirable to exercise the lower portion of the body in unison with the upper portion of the body. The second pivoting support means may include first and second pivoting leg support members for independently supporting the legs of a patient. The first and second pivoting support means of one preferred embodiment are substantially similar and have a substantially planar, rectangular configuration. The pivoting supports of this embodiment are hingeably connected about one end to opposing sides of the stationary support means with a plurality of hinges. The first and second pivoting support displacement means are connected to the first and second pivoting supports, respectively, proximate the bottom side. In the above-mentioned embodiment wherein the first pivoting support means is designed to be engaged by the patient's head, the first pivoting support means includes a member configured to restrain a patient's head, the restraining member being slidably connected to an arm pivotally connected to the first stationary support means. The pivoting supports of the preferred embodiment are fabricated from a rigid material such as wood or sheet metal. A cushion may be provided to cover the pivoting supports for the comfort of the patient.

A drive means is provided for selectively oscillating the first and second pivoting support means and is capable of so oscillating the first and second pivoting support means simultaneously. The drive means is powered by a selected motor commonly used in the art, the speed of the motor being variably controlled. A transmission is connected between the motor and a drive shaft for controlling the rotational velocity of the drive shaft in relation to the rotational velocity of the motor. The drive shaft is connected to at least one pivoting support displacement means. The drive means of the preferred embodiment is connected to at least one lateral support member of the frame means.

A pivoting support displacement means is provided for oscillating each of the first and second pivoting supports, or in the alternate embodiment, the first pivoting support and the first and second pivoting leg supports. In the preferred embodiment, first and second pivoting support displacement means are provided for respectively oscillating the first and second pivoting supports selectively and independently. The pivoting support displacement means may include a chain-driven gear. An axle extends from the center of the gear and engages a cam, a push rod being connected eccentrically to the cam. The push rod is also connected to the pivoting support such that as the cam is rotated, the bottom end of the push rod is moved in a circular direction, causing the top end of the push rod to move in a substantially vertical direction, thus displacing the pivoting support to which the push rod is attached. In an alternate embodiment, the cam is attached directly to the drive shaft driven by the transmission.

A displacement adjustment means is connected to the pivoting support displacement means for selectively altering the amplitude of displacement. In the preferred embodiment, a plurality of openings is defined by the cam, the openings being spaced apart radially away from the axle. The openings are configured to receive the selected bolt used to attach the push rod. The opening farthest from the axle has the greatest eccentricity and therefore will yield the greatest displacement of the pivoting support. Likewise, the opening closest the axle is the least eccentric and will therefore yield the least displacement. In another embodiment, the displacement adjustment is attached to the body support means.

A control box is provided for the location of the motor controls. The control box includes at least an on/off switch for the selective operation of the motor and a speed regulator for adjusting the speed of the motor. A patient control means is provided such that a patient may remotely control the speed of the drive means while using the device. The patient control means of the preferred embodiment is configured to be easily held by the user such that the desired exercise may be performed without requiring the patient to alter his position during exercise. The control button is designed to function at least as a remote on/off switch and conceivably as a speed control or other desired function. In the preferred embodiment, the patient control means is connected proximate the control box with a plug-in type jack or other conventional method. An emergency stopping means is provided to interrupt operation of the device when required. In the preferred embodiment, the emergency stopping means includes an on/off switch designed to override all other controls in order to arrest the movement of the pivoting supports.

A timing means is provided for monitoring the duration of exercise of the patient. In the preferred embodiment, the timing means includes a control timer operated by a pressure sensitive switch. As the patient is placed upon the device, the pressure sensitive switch is engaged and the control timer is activated to monitor the operation time. The timing means may be connected along the power supply line to deactivate the device when a selected period of operating time has lapsed.

A restraining means may be provided to prevent a patient from slipping along the surface of the body support means when the device is in operation. In the preferred embodiment, the restraining means includes at least a belt designed to be secured around the waist of the patient.

A mobilization means is provided such that the device may be easily transported. In the preferred embodiment, the mobilization means includes a plurality of casters provided with wheel locks which are commonly known in the art. Casters are attached to the frame means at least proximate each corner of the bottom of the frame means.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

Figure 1:
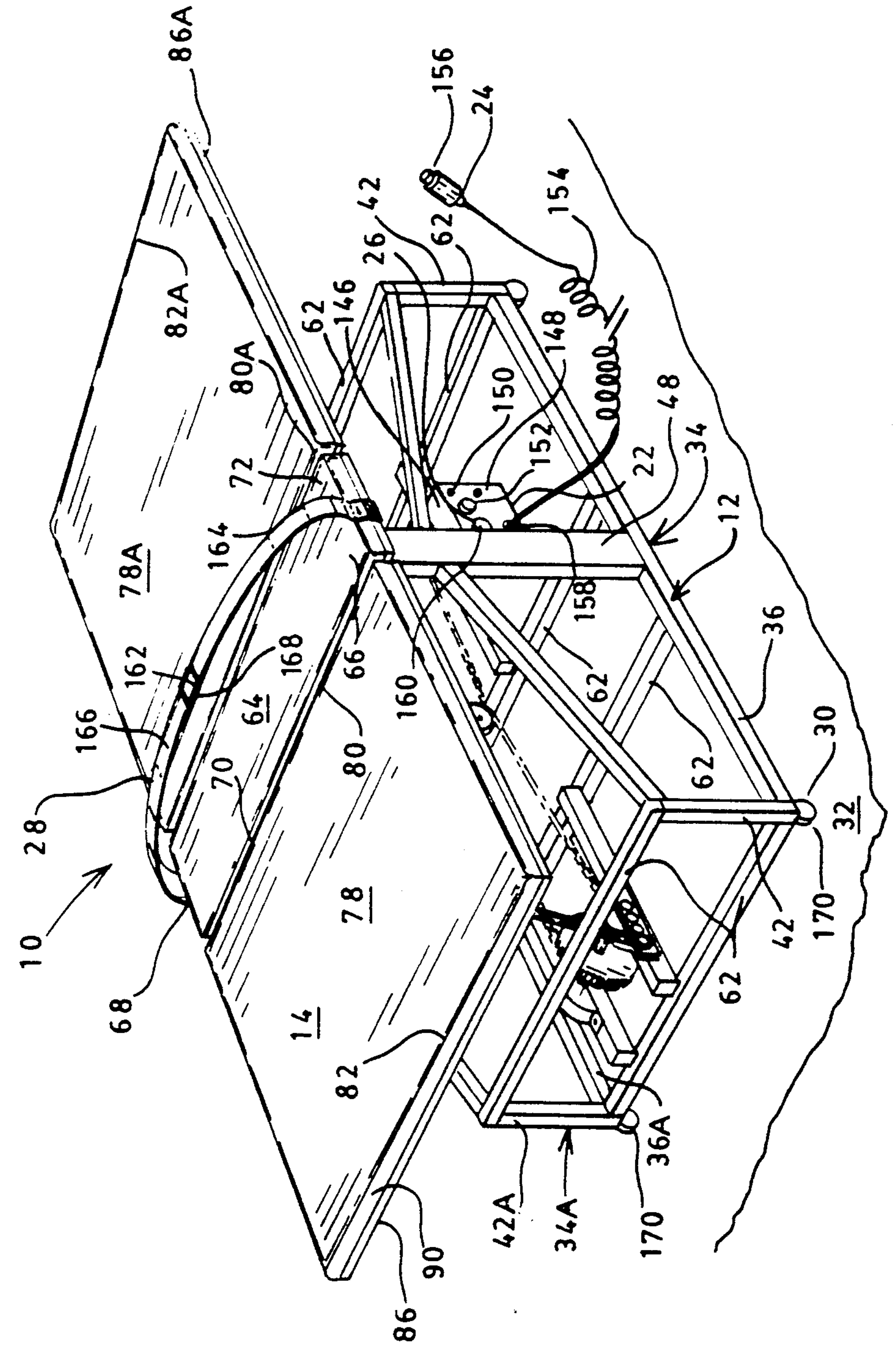
FIG. 1 is a perspective view of the improved lumbar spine therapy device constructed in accordance with several features of the present invention.
Figure 2:
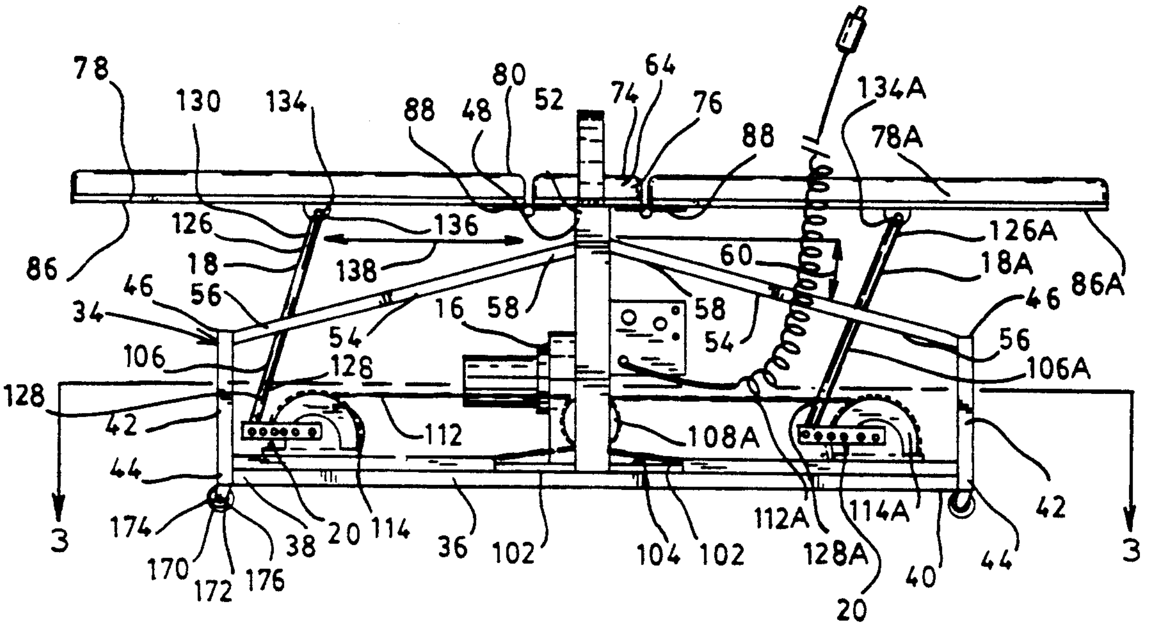
FIG. 2 illustrates a front elevation view of the improved lumbar spine therapy device shown in FIG. 1.
Figure 3:
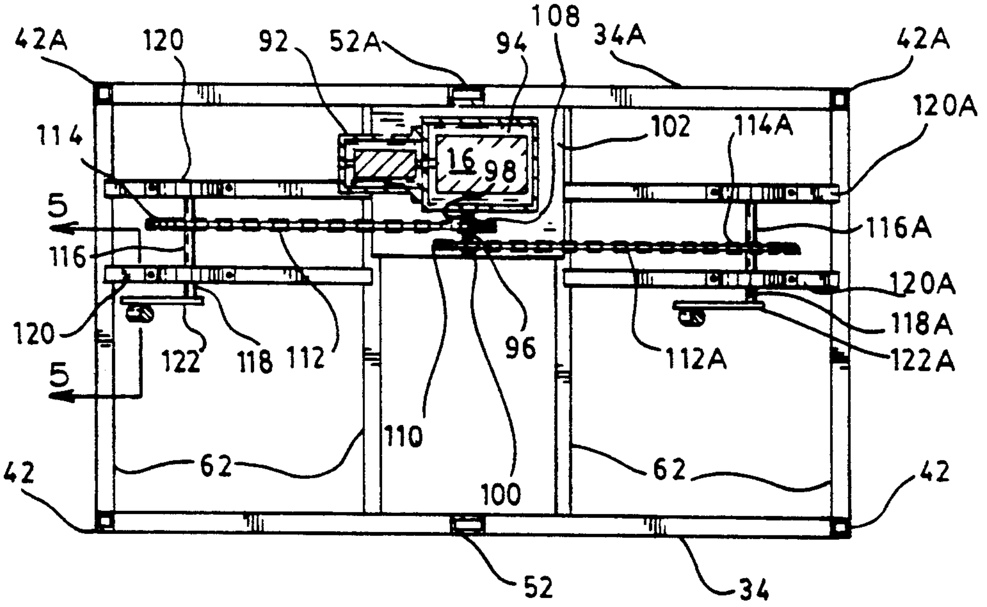
FIG. 3 is a top elevation view, in section, of the improved lumbar spine therapy device taken at 3—3 of FIG. 2.
Figure 4:
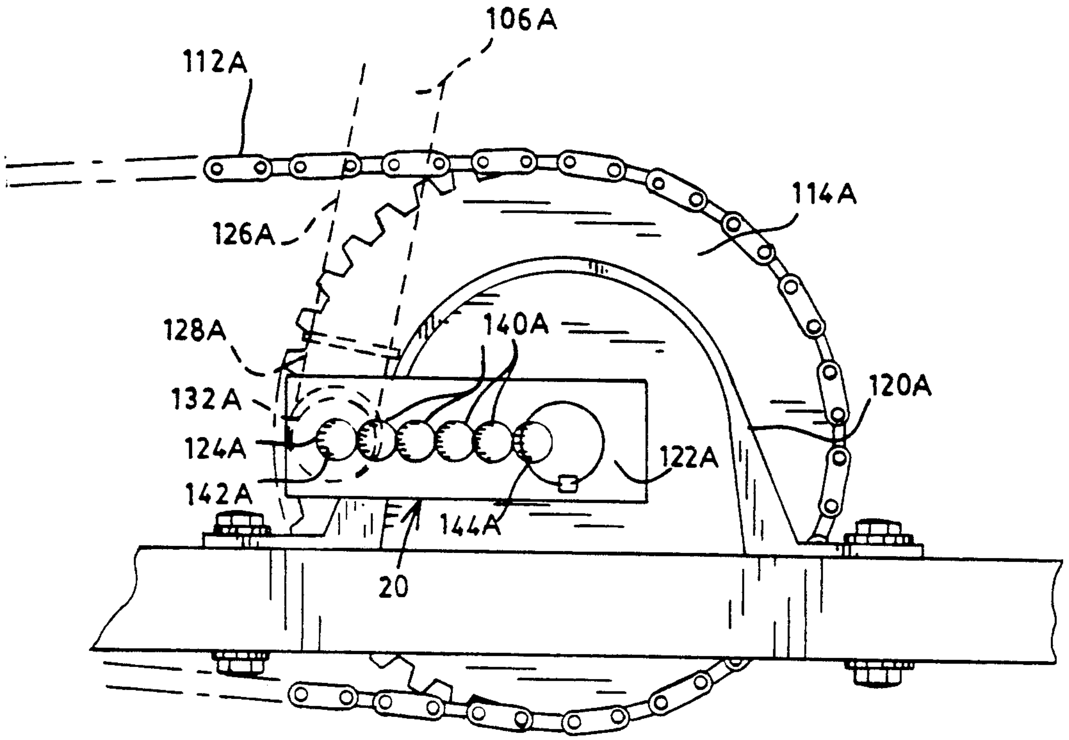
FIG. 4 illustrates a partial front elevation view of the improved lumbar spine therapy device showing the amplitude adjustment means, the push rod of the pivoting support displacement means being shown in phantom.

An improved lumbar spine therapy device incorporating various features of the present invention is illustrated generally at 10 in the figures. The improved lumbar spine therapy device 10 is designed for passively exercising the muscle groups especially surrounding the lumbar spine for postoperative and other rehabilitative therapy such as to allow normal collagen formation to occur, thus minimizing scarring and allowing a faster return to normal function and development of strength in both the muscles of function as well as the secondary support system.

The improved lumbar spine therapy device 10 includes a frame means 12 for engaging a support surface 32. The frame means 12 is fabricated from a lightweight, rigid material such as tubular steel or the like. In the preferred embodiment, the frame means 12 has a substantially box-shaped configuration with a length and width to support a selected size body support means 14. The height of the frame means 12 is dimensioned such that a patient may easily position his/her body on the body support means 14, or in the case of an inambulant patient, medical attendants may easily move the patient from a typical bed to the device 10.

The frame means 12 of the preferred embodiment includes a pair of laterally disposed faces 34 connected by a plurality of lateral braces 62. The face 34 of this embodiment has a substantially rectangular configuration including a substantially horizontal member 36. First and second upwardly extending vertical members 42 are attached to the horizontal member first and second ends 38,40 at substantial right angles. A third upwardly extending vertical member 48 is connected to the horizontal member 36 proximate the middle at a substantial right angle. The first ends 56 of first and second top members 54 are respectively connected to the second ends 46 of the first and second vertical members 42. The second ends 58 of the first and second top members 54 are connected along the third vertical member 48 proximate the second end 52 at an elevation above the top member first ends 56, the second end 52 of the third vertical member 48 extending above the first and second top member first ends 56. Thus from the top member second end 58 to the top member first ends 56, a vertical angle 60 below the horizontal is defined. The angle 60 is substantially equal to the range of motion of the body support means 14 of the improved lumbar spine therapy device 10 below the horizontal, as is discussed below. In the preferred embodiment, the angle 60 is substantially fifteen (15) degrees, but may be varied as required. For example, the angular range of motion of the legs may be desirable to be greater than that of the back for more effective exercise of the hip region. Thus, the angle 60 may be as large as thirty-five (35) degrees or larger.

In the preferred embodiment, lateral braces 62 are provided to adjoin the first and second faces 34,34A as shown or as otherwise desired. Face 34A is substantially similar to face 34 as described and is thus labelled with like numerals followed by "A". The various connections described may be of a method commonly understood such as welding or bolting, but may also include methods not yet known.

The body support means 14 is provided for supporting the body a patient. The body support means 14 includes at least one stationary support means 64 and at least one pivoting support means 78. A stationary support means 64 is provided to support the buttocks region of the patient and to act as a reference point for the displacement of the pivoting support means 78. The stationary support means 64 is connected to the seconds ends 52 of the third vertical members 48 of the frame means 12 such that the stationary support means 64 is elevated above the frame means 12. The stationary support means 64 of the preferred embodiment has a substantially rectangular configuration and is dimensioned to comfortably seat a patient of a selected size. In the preferred embodiment, the stationary support means 64 is substantially planar and is fabricated from a rigid material such as wood, sheet metal, or the like. A cushion 76 may be provided to attach to the top side 74 for the comfort of the patient, especially when extended use is required.

In one preferred embodiment, a first pivoting support means 78 is provided for supporting at least the torso of a patient. The first pivoting support means 78 of the preferred embodiment is substantially planar and has a substantially rectangular configuration. A first pivoting support means 78 of this embodiment is hingeably connected about the first end 80 to the first side 70 of the stationary support means 64 with a plurality of hinges 88. The first pivoting support displacement means 106 is connected to the first pivoting support means 78 proximate the bottom side 86, as discussed below. The first pivoting support displacement means 106 thus acts to control the elevation of the second end 82 of the first pivoting support means 78. The first pivoting support means 78 of the preferred embodiment is fabricated from a rigid material such as wood or sheet metal. A cushion 90 may be provided to cover the first pivoting support means 78 for the comfort of the patient.

A second pivoting support means 78A is provided for supporting at least the upper legs of a patient. The second pivoting means 78A is substantially similar to the first pivoting support means 78 and is thus labeled with like numerals followed by "A". The first end 80A of the second support means 78A is hingeably connected to the stationary support means 64 proximate the second side 72. The second pivoting support means 78A is connected proximate its bottom side 86A to the second pivoting support displacement means 106A in similar fashion as the first pivoting support means 78. The first and second pivoting support means 78,78A are configured such that as the first and second pivoting support displacement means 106,106A are operated, the first and second pivoting support means 78,78A oscillate simultaneously such that the feet and head of the patient are displaced the greatest distance.

A drive means 16 is provided for simultaneously oscillating the first and second pivoting support means 78,78A. The drive means 16 is powered by a selected motor 92 commonly used in the art. In the preferred embodiment, the rotational velocity of the motor 92 may be variably controlled. The first end 98 of a drive shaft 96 is connected to the motor 92, the second end 100 of the drive shaft 96 being connected to at least one pivoting support displacement means 18. In the preferred embodiment, a transmission 94 is connected between the motor 92 and the drive shaft 96 for controlling the rotational velocity of the drive shaft 96 in relation to the rotational velocity of the motor 92. The drive means 16 of the preferred embodiment is connected to the top 104 of a plate 102 with conventional means such as welding or bolting, the plate 102 being attached to at least one lateral brace 62.

A pivoting support displacement means 18 is provided for oscillating each of the first and second pivoting support means 78,78A. In the preferred embodiment, first and second pivoting support displacement means 106,106A are provided for respectively oscillating the first and second pivoting support means 78,78A selectively and independently. Either of the first and second pivoting support displacement means 106,106A may be selectively disengaged for the independent use of the other. For example, if it desired to exercise only the muscles in the region of the cervical spine, then the second pivoting support displacement means 106A may be disengaged, thereby prohibiting the exercise of the lower body.

The first and second pivoting support displacement means 106,106A are substantially similar and will therefore be referred to as "the pivoting support displacement means 106" hereafter unless otherwise required, like parts being referred to with like numerals with the designation "A" following the numbers in the drawings and description of the second pivoting support displacement means 106A. The pivoting support displacement means 106 may include a pinion 108 which is attached to the drive shaft 96 of the drive means 16 proximate the second end 100. The pinion 108 includes a sprocket 110 configured to engage a chain 112. A gear 114 is in turn driven by the chain 112. An axle 116 extends from the center of the gear 114 and is journaled to a plurality of support blocks 120, each support block 120 being attached to the frame means 12 by a conventional method. In the preferred embodiment, the axle 116 is journaled to at least two support blocks 120, at least one support block 120 being located on either side of the gear 114 to secure the axle 116 from undesired movement. A displacement cam 122 is affixed to the first end 118 of the axle 116, the cam 122 thus rotating as the gear 114 is rotated. The first end 128 of a push rod 126 is journaled to the cam 122 eccentrically such that as the cam 122 is rotated, the first end 128 of the push rod 126 is moved in a circular direction. In the preferred embodiment, the cam 122 defines a threaded opening 124 dimensioned to receive a selected bolt 132. The first end 128 of the push rod 126 has a substantial "eye" configuration dimensioned to loosely receive the selected bolt 132 inserted into the cam 122. The second end 130 of the push rod 126 is journally connected to the bottom side 86 of the pivoting support means 78 a distance 138 from the first end 80 so that as the first end 128 of the push rod 126 is moved in a circular motion, the second end 130 of the push rod 126 and the pivoting support means 78 are displaced vertically. The second end 130 of the push rod 126 of the preferred embodiment has a substantial "eye" configuration and is dimensioned to be received by a clevis 134 and held in place with a selected pin 136, bolt or the like.

Though not shown, the frame 12 defines a tab for the securement of the first end 128 of the push rod 126 when it is desired to disengage one pivoting support while oscillating the other. The tab is dimensioned to be received within the eye configuration of the push rod first end 128 and is positioned to maintain the associated pivoting support at a selected orientation during operation of the improved lumbar spine therapy device 10.

Figure 5:
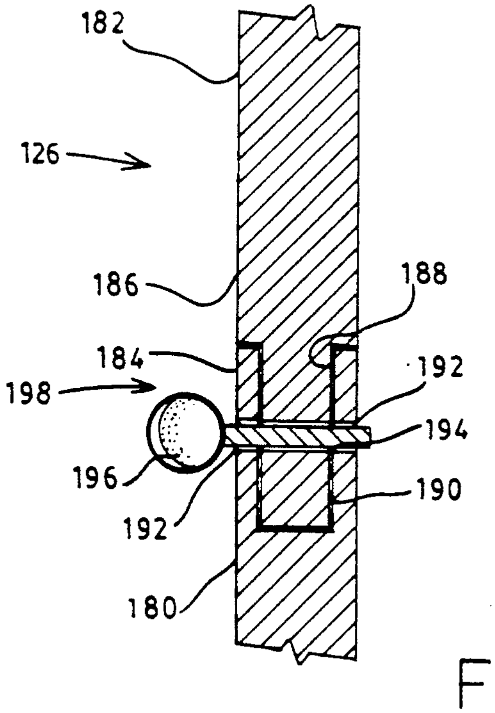
FIG. 5 is a partial front elevation view, in section, of an alternate embodiment of the push rod taken at 5—5 of FIG. 3.
Figure 6:
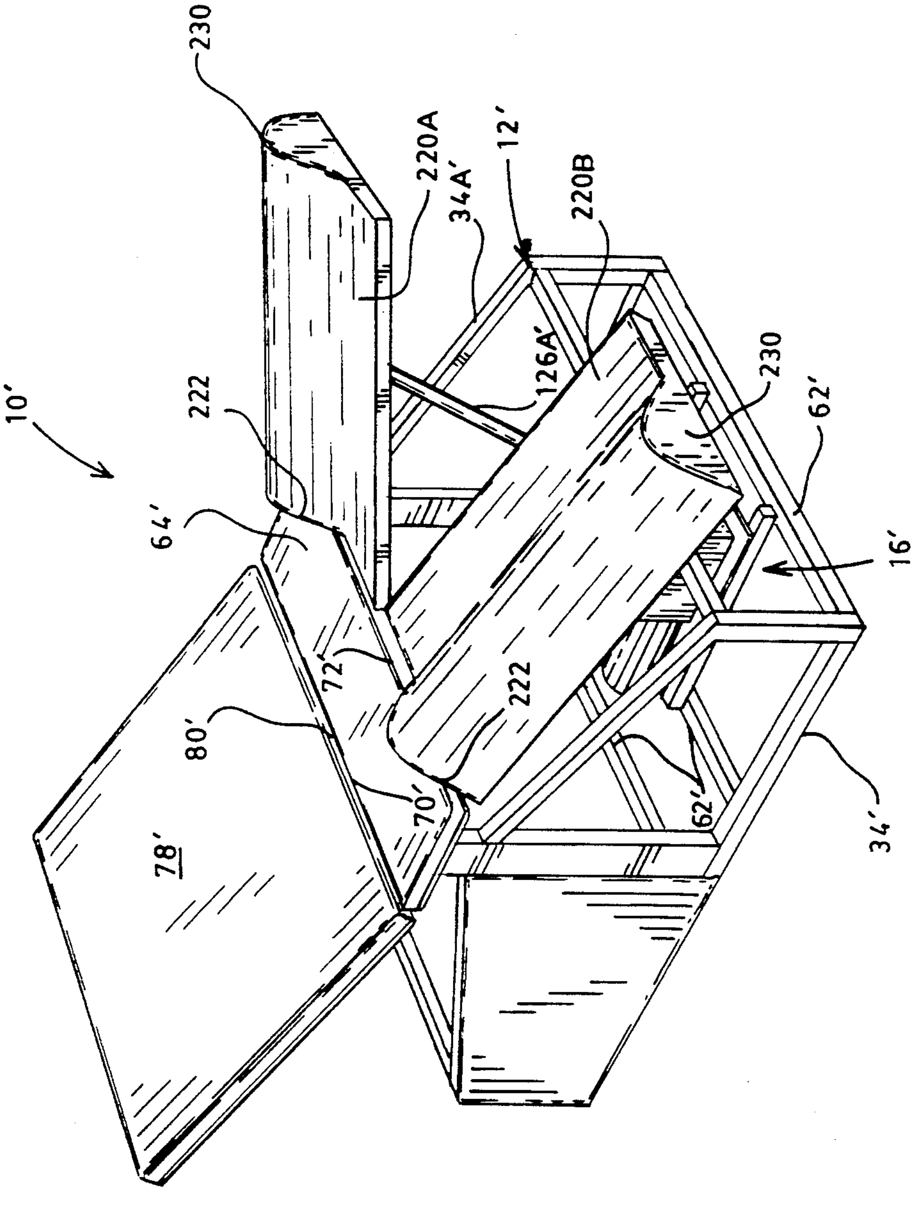
FIG. 6 is a perspective view of an alternate embodiment of the improved lumbar spine therapy device showing separate members for independently exercising the legs of a patient.
Figure 7:
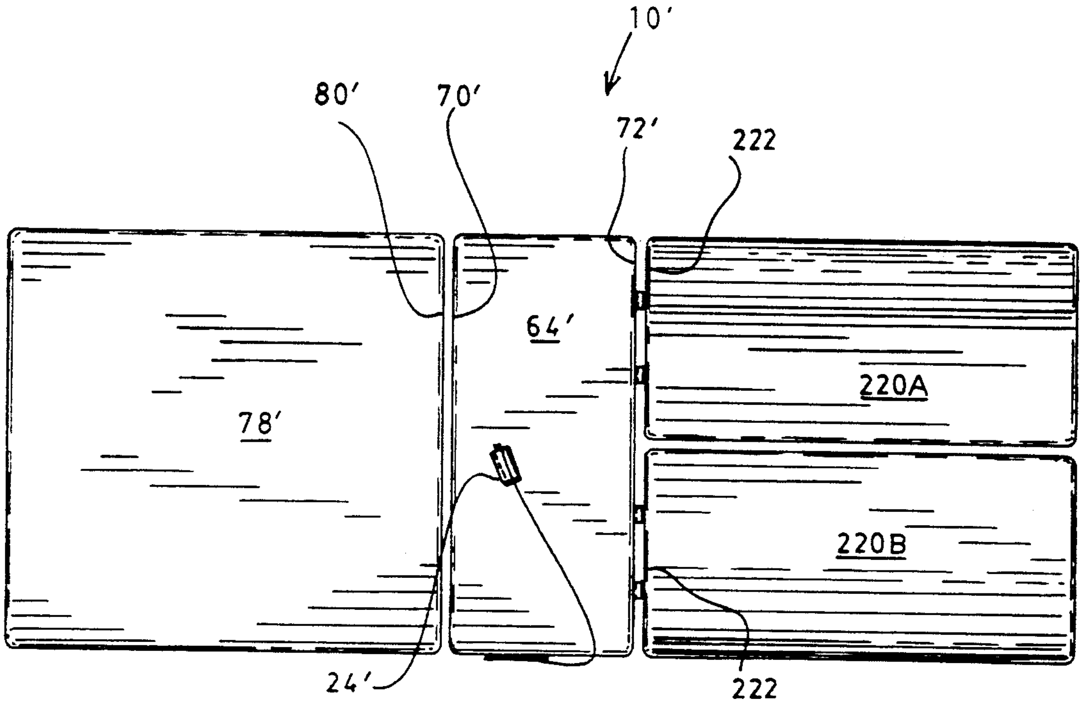
FIG. 7 illustrates a top plan view of the improved lumbar spine therapy device shown in FIG. 6.
Figure 8:
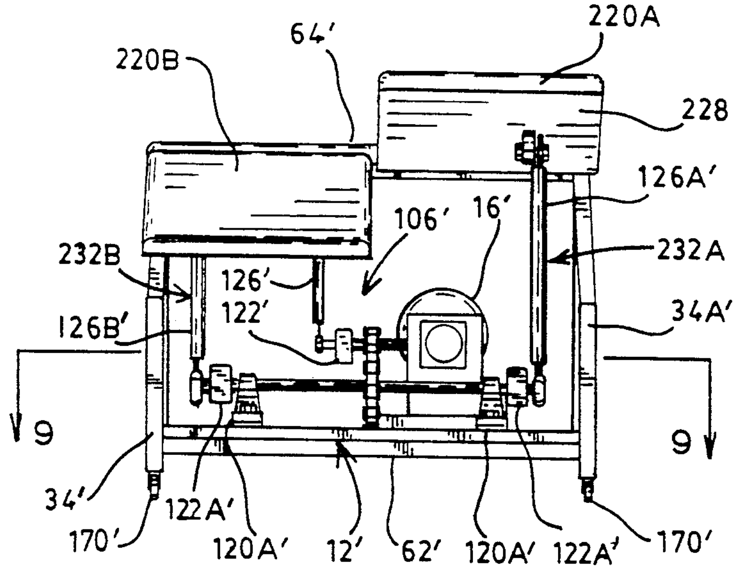
FIG. 8 is an end elevation view of the improved lumbar spine therapy device shown in FIG. 6.

In the embodiment shown in FIG. 5, the push rod 126 includes a first leg 180 and a second leg 182, the first and second legs 180,182 being connected about the second and first ends 184,186, respectively. The first leg second end 184 defines a recess 188 dimensioned to receive an extended portion 190 extending axially from the second leg first end 186 such as to define the connection 198. The connection 198 is provided as a safety feature such that an observer may selectively disengage a pivoting support means 78 simply by holding the pivoting support means second end 82 and lifting upward, thus disengaging the second leg 182 from the first leg 180. A through hole 192 may be defined proximate the first leg second end 184 to cooperate with a through hole 194 defined by the second leg extended portion 190 in order to receive a pin 196 to selectively secure the first and second legs 180,182 during transport or as otherwise required.

A displacement adjustment means 20 is connected to the pivoting support displacement means 18 for selectively altering the amplitude of displacement. In the preferred embodiment, a plurality of openings 140 is defined by the cam 122, the openings being spaced apart radially away from the axle 116. The openings 140 are threaded to receive the selected bolt 132 used to attach the push rod 126 as described above. The opening 142 spaced farthest from the axle 116 has the greatest eccentricity and therefore will yield the greatest displacement of the pivoting support means 78. Likewise, the opening 144 spaced closest to the axle 116 is the least eccentric and will therefore yield the least displacement.

Figure 11:
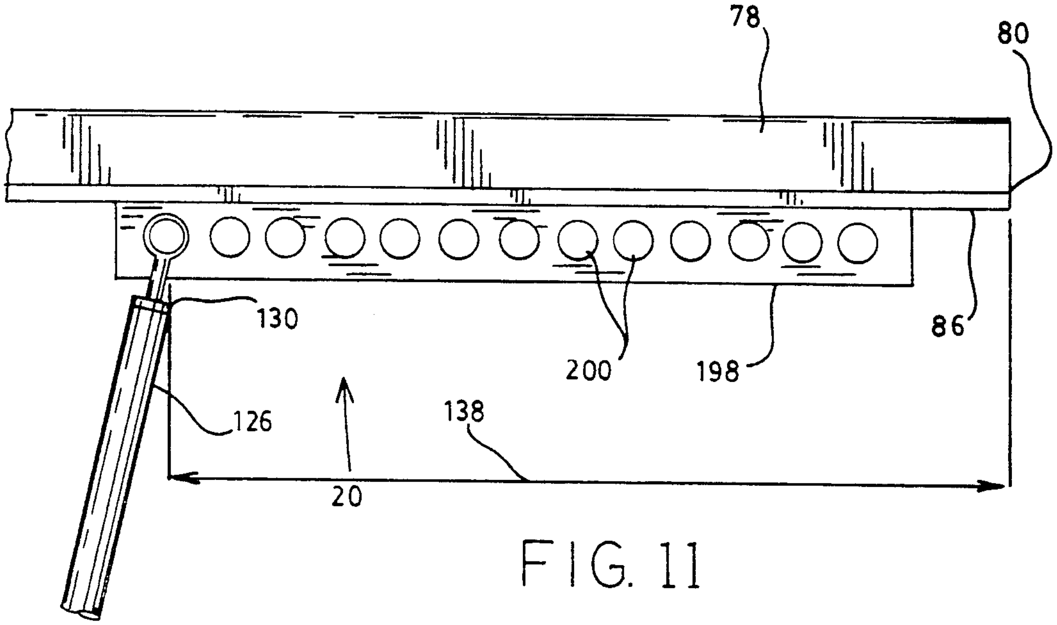
FIG. 11 is a partial front elevation showing the displacement adjusting means connected to a pivoting support means and journally connected to a push rod.
Figure 12:
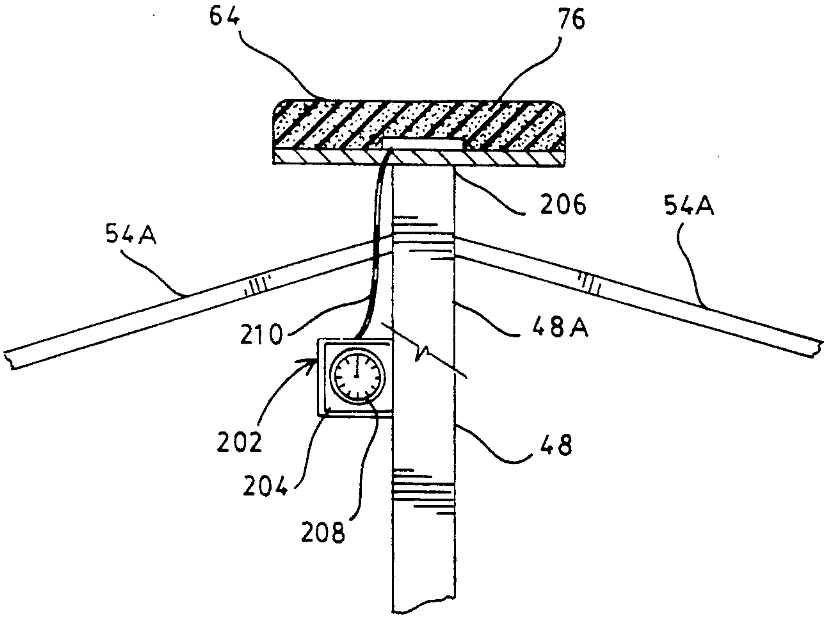
FIG. 12 is a side elevation view, partially in section, showing the timer control means.

As shown in FIG. 11, the displacement adjustment means 20 may also be connected to the pivoting support means 78 proximate the push rod second end 130, the amplitude adjustment being a resultant of varying the distance 138 between the push rod second end 130 and the pivoting support means first end 80. In this embodiment, an elongated member 198 is connected to the underneath 86 of the body support means 78 for attaching the push rod 126. The elongated member 198 defines a plurality of openings 200 spaced longitudinally apart such that the position of the push rod 126 along the body support means 78 may be selectively varied between the body support means first and second ends 80-82. In this embodiment, the greatest displacement is attained by journally connecting the push rod second end 130 with an opening 200 located along the body support means 78 such that a right angle is defined by the push rod 126 and the body support means 78 when the longitudinal axis of the push rod 126 is aligned with the center of the pivoting support displacement means 18. As the location of the push rod second end 130 is displaced from such a position, the amplitude of displacement decreases.

A control box 22 is provided for the location of the motor controls. The control box 22 includes at least an on/off switch 150 for the selective operation of the motor 92 and a speed regulator 152 for adjusting the speed of the motor 92. In the preferred embodiment, the control box 22 is connected to the frame means 12 proximate the first side panel 34 in a conventional manner such as by bolting or welding. The control box 22 of the preferred embodiment includes a junction box 146 and a cover plate 148. The junction box 146 and cover plate 148 are fabricated from a rigid or semi-rigid material such as metal or plastic. In the preferred embodiment, the junction box 146 is of a type readily available in the market.

A patient control means 24 is provided such that a patient may remotely control the speed of the drive means 16 while using the device 10. The patient control means 24 includes an extension cord 154 with a control button 156 at one end. The control button 156 of the preferred embodiment is configured to be easily held by the user such that the desired exercise may be performed without requiring the patient to alter his position during exercise. The control button 156 is designed to function at least as a remote on/off switch 150 and conceivably as a speed control 152 or other desired function. In the preferred embodiment, the patient control means 24 is connected proximate the control box 22 with a plug-in type jack 158 or other conventional method.

An emergency stopping means 26 is provided to interrupt operation of the device 10 when required. In the preferred embodiment, the emergency stopping means 26 is carried by the control box 22 and includes an on/off switch 160 designed to override all other controls in order to arrest the movement of the pivoting support means 78. The emergency stopping means 26 may be used when the patient feels an excess of discomfort or when a malfunction occurs or the patient is otherwise unable to stop the device 10.

A timing means 202 is provided for monitoring the duration of exercise of the patient. In the preferred embodiment, the timing means 202 includes a control timer 204 in electrical communication with a pressure sensitive switch 206. In this embodiment, the pressure sensitive switch 206 is connected in electrical communication through electrical conduit 210 to the stationary support means 64 such that as the patient is placed upon the device 10, the pressure sensitive switch 206 is engaged and a timing circuit (not shown) is closed. When the timing circuit is closed, the control timer 204 is activated to monitor the operation time of the device 10. In the preferred embodiment, the control timer 204 is electrically connected to the power supply of the device 10 and includes a clock-type dial 208 which may be wound to a selected time such that when the device 10 has been in operation for the selected period of time, the power will be interrupted and the device 10 will be turned off.

A restraining means 28 may be provided to prevent a patient from slipping along the body support means 14 when the device 10 is in operation. In the preferred embodiment, the restraining means 28 includes at least a belt 162 designed to be secured around the waist of the patient. The embodiment shown in the figures includes a first strap 164 connected to the first end 66 of the stationary support means 64 and a second strap 166 connected to the second end 68 of the stationary support means 64. In the preferred embodiment, the first strap 164 is releasably secured to the second strap 166 by a conventional method such as a hook-and-loop type fastener 168. The restraining means 28 is fabricated from a pliable material such as nylon or leather.

A mobilization means 30 is provided such that the device 10 may be easily transported. In the preferred embodiment, the mobilization means 30 includes a plurality of casters 170 which are commonly known in the art. In this embodiment, the casters 170 are connected to the frame means 12 such as to engage a support surface 32. Casters 170 are attached to the frame means 12 at least proximate the first ends 44 of the frame means first and second vertical members 42. The mobilization means 30 of the preferred embodiment includes braking means 172 to prevent the device 10 from unselected movement. The casters 170 of the preferred embodiment include wheel locks 172 which may be engaged by pressing one end 174 and disengaged by pressing the opposing end 176.

In an alternate embodiment shown generally in FIGS. 6-9, the improved lumbar spine therapy device 10' includes a pair of pivoting leg supports 220A,220B for pivotally supporting the left and right legs, respectively, of the patient. The pivoting leg supports 220A,220B of this embodiment are in lieu of the second pivoting support member 78A of the embodiment indicated generally at 10. Other features common to this embodiment and the embodiment described in FIGS. 1-5 will be labelled with like numerals followed with a "" symbol. Each of the pivoting leg supports 220A,220 is hinged at first ends 222 to the stationary support member 64′ as described above. The pivoting leg supports 220A,220B are connected proximate their respective bottom sides 228 to pivoting leg support displacement means 232A,232B in similar fashion as the first pivoting support means 78′. The pivoting leg supports 220A,220B may be contoured with raised portions 230 as shown to prevent a patient's legs from sliding off of the respective pivoting leg supports 220A,220B during operation of the improved lumbar spine therapy device 10′. Other contours may also be incorporated as desired.

The drive means 16′ is provided for selectively oscillating the first pivoting support means 78′ and the left and right pivoting leg supports 220A,220B. The drive means 16′ operates similarly to the drive means 16 previously described. A first pivoting support displacement means 106′ and the pivoting leg support displacement means 232A,232B are powered by the drive means 16′. The first pivoting support means 106′ operates similarly to that described previously.

Figure 9:
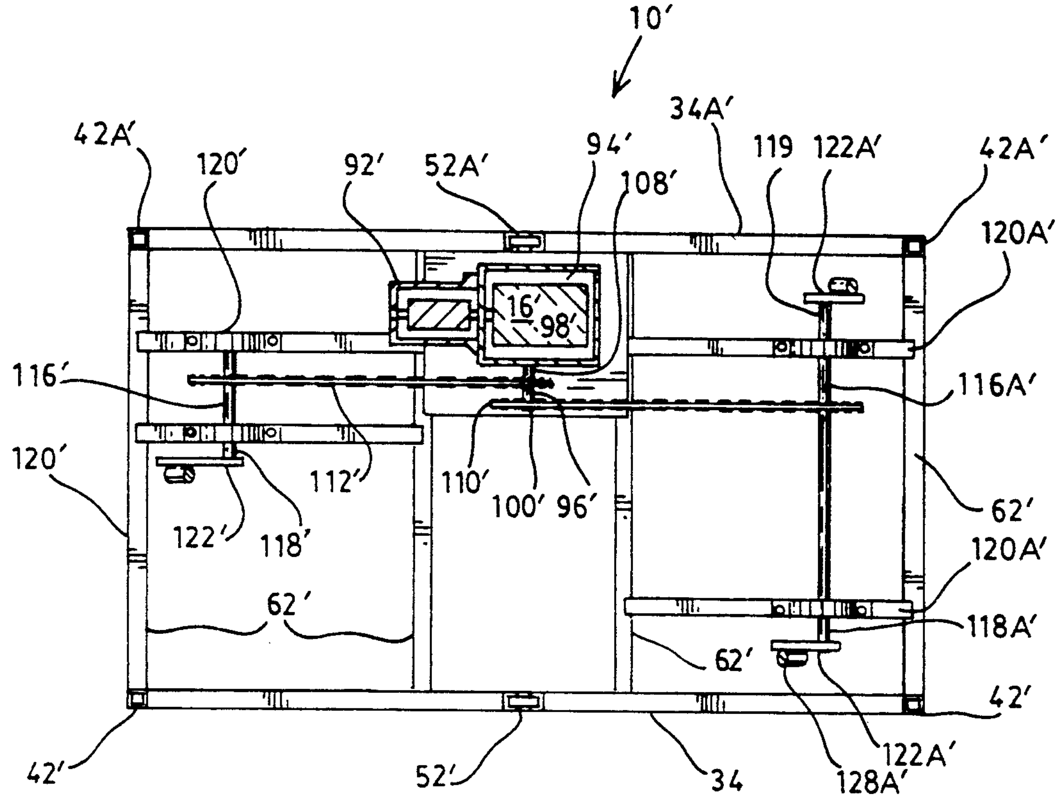
FIG. 9 is a top plan view, in section, of the improved lumbar spine therapy device, taken along lines 9—9 of FIG. 8.
Figure 10:
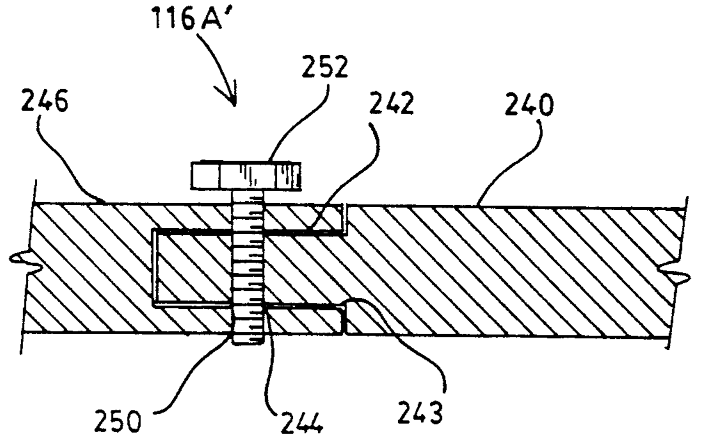
FIG. 10 is a partial side view, in section, of a drive shaft of the embodiment shown in FIG. 6.

Each of the pivoting leg support displacement means 232A,232B, as shown most clearly in FIG. 9, includes a shaft 116A′ journally supported by a plurality of support blocks 120A′, with first and second ends 118′,119 extending outwardly from the support blocks 120A′. Cams 122A′ are affixed at the first and second ends 118′,119 of the shaft 116A′ for the attachment of the first ends 128′ of push rods 126A′ as described above. As shown in FIG. 10, the shaft 116A′ of this embodiment is comprised of first and second shaft members 240,246 connected by a pin member 252. The first member 240 defines an extended portion 242 dimensioned to be received by a recess 248 defined by the second shaft member 246. Openings 244,250 are defined by the first and second shaft members 240,246, respectively, and are dimensioned to selectively receive the pin member 252. The pin may be selectively removed and the shaft members 240,246 rotated substantially 180° with respect to each other, thereby selectively placing the left and right pivoting leg supports 220A,220B in or out of phase. The push rods 126A′ are configured and function substantially as described above.

The cams 122A′ define a plurality of openings 140A′ as described previously for the attachment of the push rods 126A′ at selectable eccentric locations for adjusting the range of motion attained during the operation of the improved lumber spine therapy device 10′. Though not shown, it is envisioned that the cam 122A′ may define extended portions with openings 140A′ defined on either side of the axle 116A′. Thus, reorientation of the shaft members 240,246 may not be necessary to change the oscillation of the pivoting leg supports 220A,220B from in-phase to out-of-phase, and vice versa.

It will be seen that when the cams 122A′ are oriented such that the pivoting leg supports 220A,220B oscillate in phase, the device 10′ may be used to exercise the lumbar spine exclusively, as in the device disclosed in our earlier filed pending application, Ser. No. 07/640,945 filed on Jan. 14, 1991 (now U.S. Pat. No. 5,123,916). However, when the cams 122A′ are oriented in an out-of-phase position, the hips will be exercised as well. As before, each push rod 126′,126A′,126B′ may be selectively disengaged to prevent oscillation of the respective pivoting support 78′,220A,220B in order to better isolate selected exercise.

From the foregoing description, it will be recognized by those skilled in the art that an improved lumbar spine therapy device offering advantages over the prior art has been provided. Specifically, the improved lumbar spine therapy device provides a means for passively exercising the muscle groups especially surrounding the lumbar spine for postoperative and other rehabilitative therapy such as to allow normal collagen formation to occur, thus minimizing scarring and allowing a faster return to normal function and development of strength in both the muscles of function as well as the secondary support system. Further, the improved lumbar spine therapy device may be used to exercise the hips by independently oscillating the legs of the patient in opposite directions one from the other.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, I claim:

1. An improved lumbar spine therapy device for passively exercising the muscle groups especially surrounding the lumbar spine for postoperative and other rehabilitative therapy, said improved lumbar spine therapy device comprising:

a frame for structurally supporting any loads applied to said improved lumbar spine therapy device;

a stationary support secured to said frame for supporting the buttocks of a user;

a first pivoting support member for supporting at least the torso of said user, said support member being hingeably attached at a first end to said frame proximate a first side of said stationary support;

first and second pivoting leg support members for independently supporting at least a portion of the upper legs of said user, said pivoting leg support members each being hingeably attached at respective first ends to said frame proximate a second side of said stationary support opposite said first side;

an oscillator for oscillating said first pivoting support member about said first end through a selected angle from a horizontal plane and oscillating said first and second pivoting leg support members about said respective first ends through a further selected angle from said horizontal plane, said oscillator including a selected motor with a drive shaft connected to a first pivoting support displacement device for oscillating said first pivoting support member and to a second pivoting support displacement device for oscillating said first and second pivoting leg support members, each of said first and second pivoting support displacement devices including a pinion connected to said drive shaft, a chain pulled by said pinion, a gear driven by said chain, at least one push rod journally connected at one end to a connecting member, and a first displacement adjuster, said connecting member being fixed at one end with respect to said gear, said push rod being connected to a second end of said connecting member a selected distance from a center of said gear thereby causing said first pivoting support member and said first and second pivoting leg support members to oscillate in a substantially vertical direction, said first displacement adjuster being carried by said connecting member for selectively adjusting said selected distance from said center of said gear; and a plurality of second displacement adjusters for independently and selectively adjusting the amplitude of displacement of said first pivoting support member and said first and second pivoting leg support members, each of said plurality of second displacement adjusters being journally connected to a second end of said push rod of said first and second pivoting support displacement devices, respectively.

2. The improved lumbar spine therapy device of claim 1 wherein each of said plurality of second displacement adjusters includes an elongated member connected to one of said first pivoting support member and said first and second pivoting leg support members, said elongated member defining a plurality of openings for attaching said second end of said push rod, said openings being spaced along said elongated member in a direction away from said stationary support member and dimensioned to be journally connected to said second end of said push rod.

3. The improved lumbar spine therapy device of claim 1 wherein said selected angle and said further angle from said horizontal plane is substantially equal above said horizontal plane and below said horizontal plane.

4. An improved lumbar spine therapy device for passively exercising the muscle groups especially surrounding the lumbar spine for postoperative and other rehabilitative therapy, said improved lumbar spine therapy device comprising:

a frame for structurally supporting any loads applied to said improved lumbar spine therapy device;

a stationary support secured to said frame for supporting the buttocks of a user;

a first pivoting support member for supporting at least the torso of said user, said support member being hingeably attached at a first end to said frame proximate a first side of said stationary support;

first and second pivoting leg support members for independently supporting at least a portion of the upper legs of said user, said pivoting leg support members each being hingeably attached at respective first ends to said frame proximate a second side of said stationary support opposite said first side;

an oscillator for simultaneously oscillating said first pivoting support member about said first end through a selected angle from a horizontal plane and oscillating said first and second pivoting leg support members about said respective first ends through a further selected angle from said horizontal plane, said oscillator including a selected motor with a drive shaft connected to a first pivoting support displacement device for oscillating said first pivoting support member and to a second pivoting support displacement device for oscillating said first and second pivoting leg support members, each of said first and second pivoting support displacement devices including a pinion connected to said drive shaft, a chain pulled by said pinion, a gear driven by said chain, at least one push rod journally connected at one end to a connecting member, and a first displacement adjuster, said connecting member being fixed at one end with respect to said gear, said push rod being connected to a second end of said connecting member a selected distance from a center of said gear thereby causing said first pivoting support member and said first and second pivoting leg support members to oscillate in a substantially vertical direction, said first displacement adjuster being carried by said connecting member for selectively adjusting said selected distance from said center of said gear, said selected angle from said horizontal plane being substantially above said horizontal plane and below said horizontal plane;

a plurality of second displacement adjusters for independently and selectively adjusting the amplitude of displacement of said first pivoting support member and said first and second pivoting leg support members, each of said plurality of second displacement adjusters being journally connected to a second end of said push rod of said first and second pivoting support displacement devices, respectively, each of said plurality of second displacement adjusters including an elongated member connected to one of said first pivoting support member and said first and second pivoting leg support members, said elongated member defining a plurality of openings for attaching said second end of said push rod, said openings being spaced along said elongated member in a direction away from said stationary support member and dimensioned to be journally connected to said second end of said push rod; and mechanism within said second pivoting support displacement device for selecting in phase and out of phase oscillation of said first and second pivoting leg support members.

5. The improved lumbar spine therapy device of claim 4 further comprising a patient control device for allowing a patient to remotely and selectively vary a speed of said oscillator.

6. The improved lumbar spine therapy device of claim 4 further comprising an emergency stopping device for stopping said oscillator as required.

7. The improved lumbar spine therapy device of claim 4 further comprising a timer for controlling a time of operation of said improved lumbar spine therapy device.

8. The improved lumbar spine therapy device of claim 7 wherein said timer includes a sensor for preventing operation of said improved lumbar spine therapy device when no patient is supported thereupon.

9. An improved lumbar spine therapy device for passively exercising the muscle groups especially surrounding the lumbar spine for postoperative and other rehabilitative therapy, said improved lumbar spine therapy device comprising:

a frame for structurally supporting any loads applied to said improved lumbar spine therapy device;

a stationary support secured to said frame for supporting the buttocks of a user;

a first pivoting support member for supporting at least the torso of said user, said support member being hingeably attached at a first end to said frame proximate a first side of said stationary support;

first and second pivoting leg support members for independently supporting at least a portion of the upper legs of said user, said pivoting leg support members each being hingeably attached at respective first ends to said frame proximate a second side of said stationary support opposite said first side;

an oscillator for simultaneously oscillating said first pivoting support member about said first end through a selected angle from a horizontal plane and oscillating said first and second pivoting leg support members about said respective first ends through a further selected angle from said horizontal plane, said oscillator including a selected motor with a drive shaft connected to a first pivoting support displacement device for oscillating said first pivoting support member and to a second pivoting support displacement device for oscillating said first and second pivoting leg support members, each of said first and second pivoting support displacement devices including a pinion connected to said drive shaft, a chain pulled by said pinion, a gear driven by said chain, at least one push rod journally connected at one end to a connecting member, and a first displacement adjuster, said connecting member being fixed to said gear, said push rod being connected to a second end of said connecting member a selected distance from a center of said gear thereby causing said first pivoting support member and said first and second pivoting leg support members to oscillate in a substantially vertical direction, said first displacement adjuster being carried by said connecting member for selectively adjusting said selected distance from said center of said gear, said selected angle from said horizontal plane being substantially equal above said horizontal plane and below said horizontal plane;

said second pivoting support displacement device including a transverse shaft rotated by said chain, said shaft having first and second axially-aligned portions, said first portion provided with an axial recess in one end defining a surrounding wall, said second portion provided with an axial extension to be closely received within said recess, said surroundings wall and said extension provided with aligned passages extending transverse to an axis of said shaft, and with a releasable pin extending through said aligned passages whereby, with said fastener removed from said passages, said first and second shaft portions can be axially rotated with respect to each other to select in phase and out of phase oscillation of said first and second pivoting leg support members;

a plurality of second displacement adjusters for independently and selectively adjusting the amplitude of displacement of said first pivoting support member and said first and second pivoting leg support members, each of said plurality of second displacement adjusters being journally connected to a second end of said push rod of said first and second pivoting support displacement devices, respectively, each of said plurality of second displacement adjusters including an elongated member connected to one of said first pivoting support member and said first and second pivoting leg support members, said elongated member defining a plurality of openings for attaching said second end of said push rod, said openings being spaced along said elongated member in a direction away from said stationary support member and dimensioned to be journally connected to said second end of said push rod;

a patient control device for allowing a patient to remotely and selectively vary a speed of said oscillator;

an emergency stopping device for stopping said oscillator as required; and a timer for controlling a time of operation of said improved lumbar spine therapy device, said timer including a sensor for preventing operation of said improved lumbar spine therapy device when no patient is supported thereupon.

10. The improved lumbar spine therapy device of claim 9 further comprising a restraining device for securing said patient from falling from said improved lumbar spine therapy device while said improved lumbar spine therapy device is in operation and to prevent said patient from slipping on said improved lumbar spine therapy device when in operation.

11. The lumber spine therapy device of claim 9 further comprising a mobilization device for enabling said improved lumbar spine therapy device to be easily transported as desired.

12. The improved lumbar spine therapy device of claim 4 wherein said mechanism for selecting in phase and out of phase oscillation of said first and second pivoting leg support members comprises:

a transverse shaft within said second pivoting support displacement device having first and second axially aligned portions, said first shaft portion provided with an axial recess within one end to define a surrounding wall, said second shaft portion provided with an axial extension at one end to be received within said recess, said surrounding wall and said extension provided with aligned passages transverse to an axis of said shaft ;and a removable pin engaged with said aligned passages;

whereby, with said pin removed, said first and second shaft portions can be rotated 180°, and the pin replaced to select said in phase and out of phase oscillation of said first and second pivoting leg support members.

13. The improved lumbar spine therapy device of claim 1 wherein said oscillator simultaneously oscillates said first pivoting support member and said first and second pivoting leg support members.

14. The improved lumbar spine therapy device of claim 4 wherein said oscillator simultaneously oscillates said first pivoting support member and said first and second pivoting leg support members.

* * * * *